United States Patent [19]
Schiff et al.

[11] Patent Number: 5,800,388
[45] Date of Patent: Sep. 1, 1998

[54] PLUNGER/RAM ASSEMBLY ADAPTED FOR A FLUID INJECTOR

[75] Inventors: David Schiff, Highland Park, N.J.; Paul Mulhauser, New York, N.Y.

[73] Assignee: Medi-Ject Corporation, Minneapolis, Minn.

[21] Appl. No.: 609,140

[22] Filed: Feb. 29, 1996

[51] Int. Cl.$^6$ .................................................. A61M 5/30
[52] U.S. Cl. ........................................... 604/68; 604/49
[58] Field of Search ............................ 604/68, 135, 49, 604/69, 70, 134, 143

[56] References Cited

U.S. PATENT DOCUMENTS

| D. 304,616 | 11/1989 | Dunlap et al. |
|---|---|---|
| D. 349,958 | 8/1994 | Hollis et al. |
| 396,107 | 1/1889 | Nickerson |
| 489,757 | 1/1893 | Reilly |
| 1,567,517 | 12/1925 | Kisbey |

(List continued on next page.)

FOREIGN PATENT DOCUMENTS

| 2028870 | 5/1991 | Canada |
|---|---|---|
| 2071115 | 12/1992 | Canada |
| 0 157 906 | 10/1985 | European Pat. Off. |
| 0 460 961 | 6/1991 | European Pat. Off. |
| 76202162 | 5/1986 | Taiwan |
| 959397 | 6/1964 | United Kingdom |
| WO 93/03779 | 3/1993 | WIPO |
| WO 95/03844 | 2/1995 | WIPO |
| WO 96/21482 | 7/1996 | WIPO |

OTHER PUBLICATIONS

Catalog: Hoechst Celanese—Advanced Materials Group, "Vectra® Liquid Crystal Polymer".
Catalog: Industrial Gas Springs, Ltd.

*Primary Examiner*—Michael Buiz
*Assistant Examiner*—Kevin Truong
*Attorney, Agent, or Firm*—Pennie & Edmonds LLP

[57] ABSTRACT

A plunger/ram assembly adapted for a hypodermic fluid injector having a nozzle body defining a fluid chamber and an orifice communicating with the chamber. The plunger/ram assembly comprises a plunger adapted to be movably positioned in the chamber and a ram assembly. The ram assembly is operatively connected to the plunger for drawing fluid into and expelling fluid out the chamber through the orifice. The ram assembly includes first and second driving members spaced apart by a preselected free travel distance and a resilient biasing member having a preselected preload. The resilient biasing member is operatively disposed for maintaining the free travel distance when the preload is greater than a force applied to the first driving member. The maximum fluid pressure generated by the plunger/ram assembly is controlled by a free travel distance or gap existing between first and second driving members before the injector is fired. Prior to firing, the gap is accurately maintained during movement of the plunger/ram assembly by a resilient spring member. This arrangement ensures that the injected fluid will be delivered to the patient's body at a desired pressure sufficient to properly pierce the patient's skin or the like.

17 Claims, 9 Drawing Sheets

U.S. PATENT DOCUMENTS

| | | |
|---|---|---|
| 1,973,706 | 9/1934 | Hawley . |
| 2,322,244 | 6/1943 | Lockhart . |
| 2,322,245 | 6/1943 | Lockhart . |
| 2,380,534 | 7/1945 | Lockhart . |
| 2,390,246 | 12/1945 | Folkman . |
| 2,398,544 | 4/1946 | Lockhart . |
| 2,413,303 | 12/1946 | Folkman . |
| 2,459,875 | 1/1949 | Folkman . |
| 2,547,099 | 4/1951 | Smoot . |
| 2,605,763 | 8/1952 | Smoot . |
| 2,635,602 | 4/1953 | Hein . |
| 2,653,602 | 9/1953 | Smoot . |
| 2,670,121 | 2/1954 | Scherer et al. . |
| 2,671,347 | 3/1954 | Scherer . |
| 2,681,653 | 6/1954 | Kuhne . |
| 2,688,968 | 9/1954 | Scherer . |
| 2,699,166 | 1/1955 | Dickinson, Jr. et al. . |
| 2,704,542 | 3/1955 | Scherer . |
| 2,704,543 | 3/1955 | Scherer . |
| 2,705,953 | 4/1955 | Potez . |
| 2,714,887 | 8/1955 | Venditty . |
| 2,717,597 | 9/1955 | Hein, Jr. . |
| 2,737,946 | 3/1956 | Hein, Jr. . |
| 2,754,818 | 7/1956 | Scherer . |
| 2,762,369 | 9/1956 | Venditty . |
| 2,762,370 | 9/1956 | Venditty . |
| 2,764,977 | 10/1956 | Ferguson . |
| 2,789,839 | 4/1957 | Siebert . |
| 2,798,485 | 7/1957 | Hein, Jr. . |
| 2,798,486 | 7/1957 | Hein, Jr. . |
| 2,800,903 | 7/1957 | Smoot . |
| 2,816,543 | 2/1957 | Venditty et al. . |
| 2,816,544 | 12/1957 | Scherer et al. . |
| 2,820,655 | 1/1958 | Hilemam . |
| 2,821,193 | 1/1958 | Ziherl et al. . |
| 2,821,981 | 2/1958 | Ziherl et al. . |
| 2,825,332 | 3/1958 | Johnson . |
| 2,902,994 | 9/1959 | Scherer . |
| 2,921,582 | 1/1960 | Sadd . |
| 2,928,390 | 3/1960 | Venditty et al. . |
| 3,057,349 | 10/1962 | Ismach . |
| 3,066,670 | 12/1962 | Stauffer . |
| 3,115,133 | 12/1963 | Morando . |
| 3,123,070 | 3/1964 | Kath . |
| 3,129,708 | 4/1964 | Krantz . |
| 3,130,723 | 4/1964 | Venditty et al. . |
| 3,131,692 | 5/1964 | Love . |
| 3,138,157 | 6/1964 | Ziherl et al. . |
| 3,140,713 | 7/1964 | Ismach . |
| 3,147,967 | 9/1964 | Bougeard . |
| 3,167,071 | 1/1965 | Venditty . |
| 3,189,029 | 6/1965 | Stephens . |
| 3,202,151 | 8/1965 | Kath . |
| 3,245,703 | 4/1966 | Manly . |
| 3,292,622 | 12/1966 | Banker . |
| 3,308,818 | 3/1967 | Rutkowski . |
| 3,330,276 | 7/1967 | Gordon . |
| 3,330,277 | 7/1967 | Gabriels . |
| 3,335,722 | 8/1967 | Lowry et al. . |
| 3,353,537 | 11/1967 | Knox et al. . |
| 3,406,684 | 10/1968 | Tsujino . |
| 3,424,154 | 1/1969 | Kinsley . |
| 3,461,867 | 8/1969 | Zimmet et al. . |
| 3,476,110 | 11/1969 | Yahner . |
| 3,490,451 | 1/1970 | Yahner . |
| 3,507,276 | 4/1970 | Burgess . |
| 3,518,990 | 7/1970 | Banker . |
| 3,521,633 | 7/1970 | Yahner . |
| 3,526,225 | 9/1970 | Isobe . |
| 3,527,212 | 9/1970 | Clark . |
| 3,557,784 | 1/1971 | Shields . |
| 3,561,443 | 2/1971 | Banker . |
| 3,625,208 | 12/1971 | Frost et al. . |
| 3,659,587 | 5/1972 | Baldwin . |
| 3,688,765 | 9/1972 | Gasaway . |
| 3,714,943 | 2/1973 | Yanof et al. . |
| 3,768,472 | 10/1973 | Hodosh et al. . |
| 3,779,371 | 12/1973 | Rovinski . |
| 3,782,380 | 1/1974 | Van Der Gaast . |
| 3,783,895 | 1/1974 | Weichselbaum . |
| 3,788,315 | 1/1974 | Laurens . |
| 3,805,783 | 4/1974 | Ismach . |
| 3,827,601 | 8/1974 | Magrath et al. . |
| 3,838,689 | 10/1974 | Cohen . |
| 3,908,651 | 9/1975 | Fudge . |
| 3,938,520 | 2/1976 | Scislowicz et al. . |
| 3,945,379 | 3/1976 | Pritz et al. . |
| 3,945,383 | 3/1976 | Bennett et al. . |
| 4,059,107 | 11/1977 | Iriguchi et al. . |
| 4,089,334 | 5/1978 | Schwebel et al. . |
| 4,141,675 | 2/1979 | O'Neill .................................. 417/214 |
| 4,328,802 | 5/1982 | Curley et al. . |
| 4,387,879 | 6/1983 | Tauschinski . |
| 4,421,508 | 12/1983 | Cohen . |
| 4,447,225 | 5/1984 | Taff et al. . |
| 4,500,075 | 2/1985 | Tsuchiya et al. . |
| 4,505,709 | 3/1985 | Froning et al. . |
| 4,507,113 | 3/1985 | Dunlap . |
| 4,518,385 | 5/1985 | Lindmayer et al. . |
| 4,561,856 | 12/1985 | Cochran . |
| 4,588,403 | 5/1986 | Weiss et al. . |
| 4,596,556 | 6/1986 | Morrow et al. . |
| 4,619,651 | 10/1986 | Kopfer et al. . |
| 4,623,332 | 11/1986 | Lindmayer et al. . |
| 4,626,242 | 12/1986 | Fejes et al. . |
| 4,662,878 | 5/1987 | Lindmayer . |
| 4,675,020 | 6/1987 | McPhee . |
| 4,680,027 | 7/1987 | Parsons et al. . |
| 4,709,686 | 12/1987 | Taylor et al. . |
| 4,722,728 | 2/1988 | Dixon . |
| 4,744,786 | 5/1988 | Hooven . |
| 4,768,568 | 9/1988 | Fournier et al. . |
| 4,771,758 | 9/1988 | Taylor et al. . |
| 4,775,173 | 10/1988 | Sauer . |
| 4,790,824 | 12/1988 | Morrow et al. . |
| 4,834,149 | 5/1989 | Fournier et al. . |
| 4,850,967 | 7/1989 | Cosmai . |
| 4,863,427 | 9/1989 | Cocchi . |
| 4,874,367 | 10/1989 | Edwards . |
| 4,883,483 | 11/1989 | Lindmayer . |
| 4,909,488 | 3/1990 | Seiber et al. . |
| 4,923,072 | 5/1990 | Rilliet . |
| 4,940,460 | 7/1990 | Casey et al. . |
| 4,941,880 | 7/1990 | Burns . |
| 4,948,104 | 8/1990 | Wirges . |
| 4,950,240 | 8/1990 | Greenwood et al. ................... 604/110 |
| 4,989,905 | 2/1991 | Rajecki . |
| 5,024,656 | 6/1991 | Gasaway et al. ......................... 604/70 |
| 5,031,266 | 7/1991 | Tillman et al. . |
| 5,041,715 | 8/1991 | Muller . |
| 5,061,263 | 10/1991 | Yamazaki et al. . |
| 5,062,830 | 11/1991 | Dunlap . |
| 5,064,413 | 11/1991 | McKinnon et al. . |
| 5,066,280 | 11/1991 | Braithwaite . |
| 5,073,165 | 12/1991 | Edwards . |
| 5,085,332 | 2/1992 | Gettig et al. . |
| 5,116,313 | 5/1992 | McGregor . |
| 5,135,507 | 8/1992 | Haber et al. . |
| 5,161,786 | 11/1992 | Cohen . |
| 5,165,560 | 11/1992 | Ennis, III et al. . |
| 5,176,406 | 1/1993 | Straghan . |
| 5,181,912 | 1/1993 | Hammett ................................ 604/110 |

| | | | | | | |
|---|---|---|---|---|---|---|
| 5,188,599 | 2/1993 | Botich et al. ............ 604/110 | | 5,360,146 | 11/1994 | Ikushima . |
| 5,190,523 | 3/1993 | Lindmayer . | | 5,383,851 | 1/1995 | McKinnon, Jr. et al. . |
| 5,193,517 | 3/1993 | Taylor et al. . | | 5,399,163 | 3/1995 | Peterson et al. . |
| 5,209,362 | 5/1993 | Lutzker . | | 5,407,431 | 4/1995 | Botich et al. . |
| 5,224,932 | 7/1993 | Lappas . | | 5,413,471 | 5/1995 | Yamauchi ............ 425/129.1 |
| 5,226,882 | 7/1993 | Bates . | | 5,423,756 | 6/1995 | Van der Merwe . |
| 5,292,308 | 3/1994 | Ryan . | | 5,480,381 | 1/1996 | Weston . |
| 5,304,128 | 4/1994 | Haber et al. . | | 5,499,972 | 3/1996 | Parsons ................ 604/68 |
| 5,312,335 | 5/1994 | McKinnon et al. . | | 5,503,627 | 4/1996 | McKinnon et al. ........ 604/72 |
| 5,312,577 | 5/1994 | Peterson et al. . | | 5,520,639 | 5/1996 | Peterson et al. ........ 604/68 |
| 5,316,198 | 5/1994 | Fuchs et al. . | | 5,569,189 | 10/1996 | Parsons ................ 604/68 |
| 5,334,144 | 8/1994 | Alchas et al. . | | 5,599,302 | 2/1997 | Lilley et al. ........... 604/68 |
| 5,352,203 | 10/1994 | Vallelunga et al. ........ 604/110 | | | | |
| 5,356,380 | 10/1994 | Hoekwater et al. . | | | | |

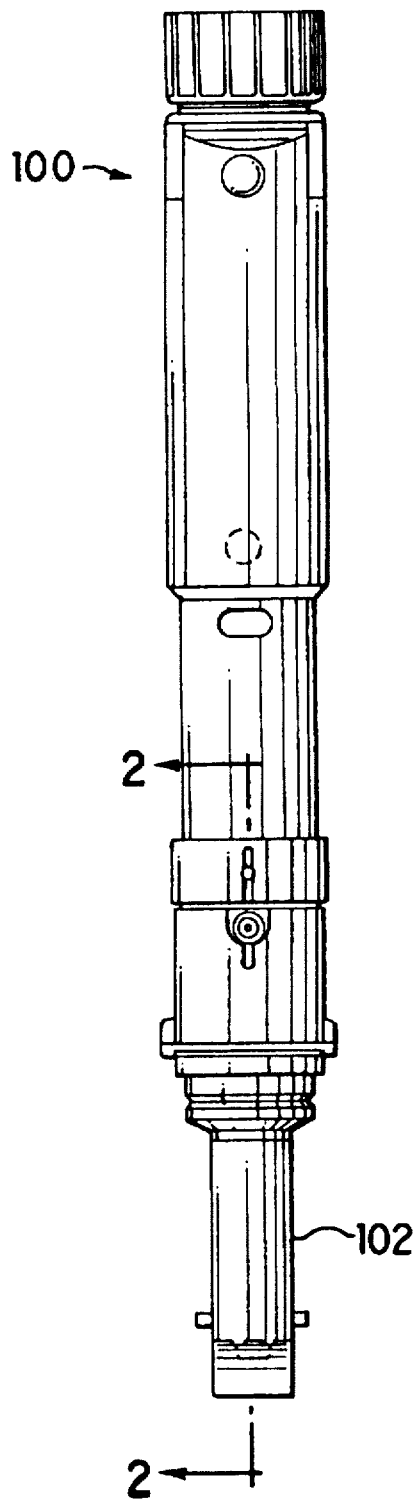
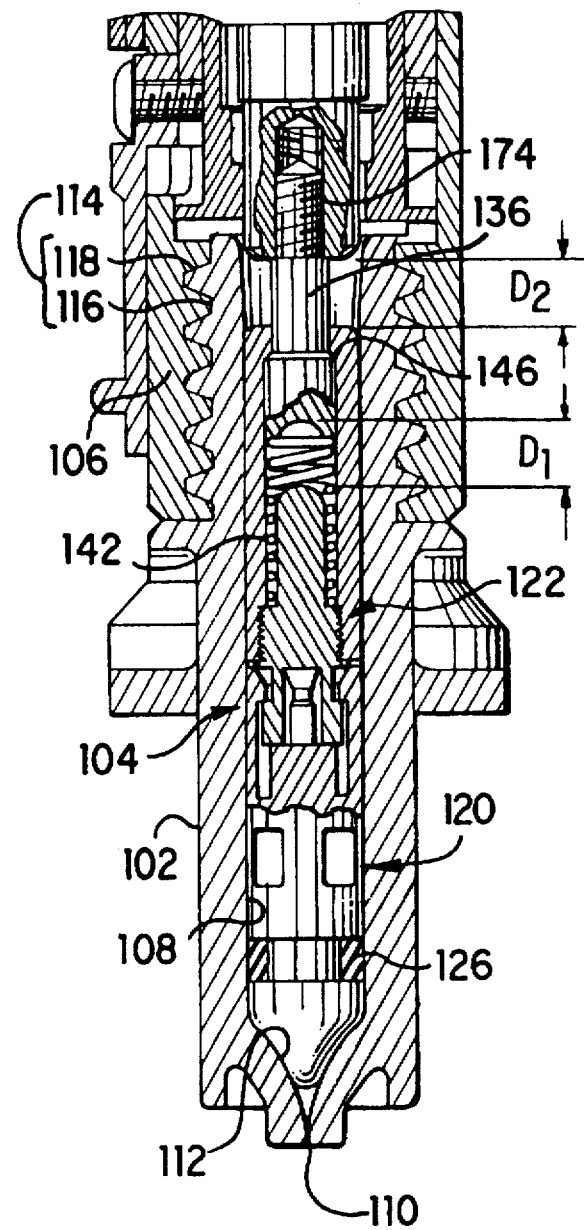
FIG. 1
FIG. 2

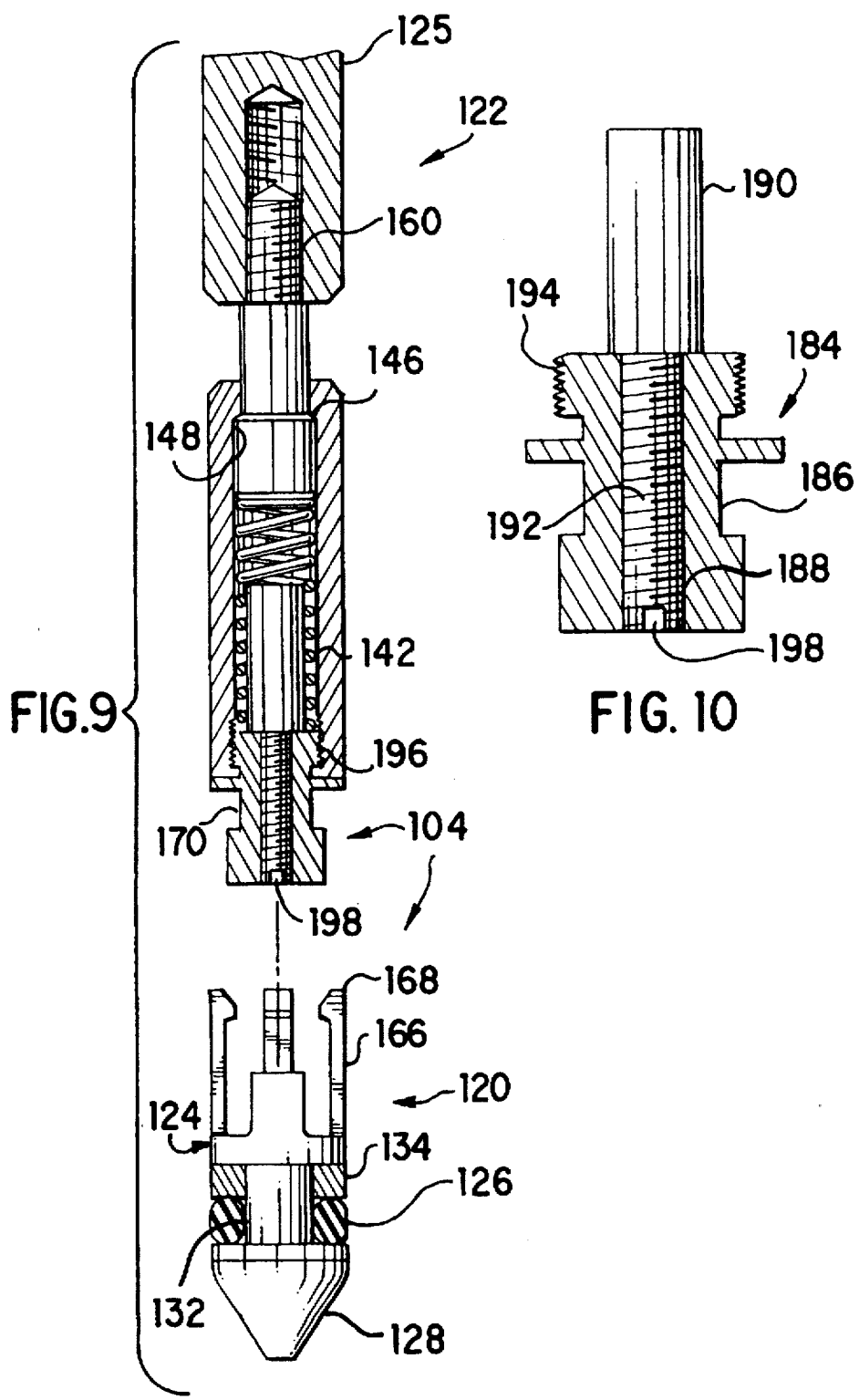

5,800,388

1

PLUNGER/RAM ASSEMBLY ADAPTED FOR A FLUID INJECTOR

TECHNICAL FIELD

The present invention generally relates to fluid injectors and, more particularly, to hypodermic fluid injectors adapted to inject a fluid selected from medication or the like into a patient.

BACKGROUND

Medical communities have become concerned over the possibility of accidental communication of disease, such as Acquired Immune Deficiency Syndrome (AIDS), hepatitis, and other diseases communicable through bodily fluids, through accidental needle sticking and improperly sterilized multiple-use needle injectors. One way to curb some of these mishaps is to employ a needleless injecting device.

Needleless injectors have no needle. They thus completely remove any apprehension or the possibility of being pierced by a contaminated needle. At least in this regard, the needleless injectors are superior in eliminating accidental disease transmission. Different needleless injector types have been contemplated, as described, for instance, in U.S. Pat. No. 5,062,830 issued to Dunlap; U.S. Pat. No. 4,790,824 to Morrow et al.; U.S. Pat. No. 4,623,332 to Lindmayer et al.; U.S. Pat. No. 4,421,508 to Cohen; U.S. Pat No. 4,089,334 to Schwebel et al.; U.S. Pat. No. 3,688,765 to Gasaway; U.S. Pat. No. 3,115,133 to Morando; U.S. Pat. No. 2,816,543 to Venditty et al.; and U.S. Pat. No. 2,754,818 to Scherer. These injectors have been contemplated to administer medication as a fine, high velocity jet, delivered under sufficient pressure to enable the jet to pass through the skin tissue without requiring a hypodermic needle. These injectors typically have a nozzle assembly which has a barrel-like nozzle body for holding medication therein. The nozzle member has an orifice through which a jet stream of medication is forced out from the chamber when a plunger/piston is fired or actuated by some type of energy source.

As disclosed in Dunlap, one method for improving the peak pressure of the jet stream is provide a predetermined gap between the plunger of the nozzle assembly and the ram of the energy source. However, there remains a need for a nozzle assembly which is capable of easily establishing and maintaining this predetermined gap after liquid medicine or the like has been drawn into the chamber and during the process of bleeding air from the chamber, prior to firing the injector.

SUMMARY OF THE INVENTION

In one aspect of the present invention, there is disclosed a plunger/ram assembly. The plunger/ram assembly is adapted for a fluid injector having a nozzle body defining a fluid chamber and an orifice communicating with the chamber. The plunger/ram assembly comprises a plunger, adapted to be movably positioned in the chamber, and a ram assembly operatively connected to the plunger for drawing fluid into and expelling fluid out the chamber through the orifice. The ram assembly includes first and second driving members spaced apart by a preselected free travel distance and a resilient biasing member having a preselected preload. The plunger is connected to the second driving member. The resilient biasing member is operatively disposed for maintaining the free travel distance when the preload is greater than a force applied to the first driving member. The second driving member can have either a fixed or an adjustable length which determines the magnitude and location of the free travel distance. The plunger may be removably connected to the second driving member.

In another aspect of the present invention, there is disclosed a fluid injector comprising a nozzle body, a plunger, and a ram assembly. The nozzle body defines a fluid chamber and an orifice communicating with the chamber. The plunger is movably positioned in said chamber and operatively connected to the ram assembly for drawing fluid into and expelling fluid out the chamber through the orifice. The ram assembly includes first and second driving members spaced apart by a preselected free travel distance and a resilient biasing member having a preselected preload. The plunger is connected to the second driving member. The resilient biasing member is operatively disposed for maintaining the free travel distance when the preload is greater than a force applied to the first driving member and for collapsing the free travel distance when the preload is smaller than a force applied to the first driving member and when resistance of the plunger to movement is greater than the force applied to the first driving member.

The maximum fluid pressure generated by the nozzle assembly is controlled by the free travel distance or gap existing before the injector is fired. Prior to firing, the free travel distance is accurately maintained during a bleed phase of operation or other movement of the plunger/ram assembly. This arrangement ensures that the injected fluid will be delivered to the patient's body at a desired pressure sufficient to properly pierce the patient's skin or the like.

BRIEF DESCRIPTION OF THE DRAWINGS

FIG. 1 is a diagrammatic elevational view of a fluid injector including a first embodiment of a plunger/ram assembly of the present invention.

FIG. 2 is a diagrammatic enlarged cross-sectional view of one end portion of the fluid injector taken along line 2—2 of FIG. 1.

FIG. 9 is a diagrammatic exploded cross-sectional view of a second embodiment of a plunger/ram assembly of the present invention.

FIG. 10 is a diagrammatic isolated enlarged partial cross-sectional view of an adjustable tip or second driving member shown in FIG. 9.

DETAILED DESCRIPTION OF THE DRAWINGS

Figure 3:
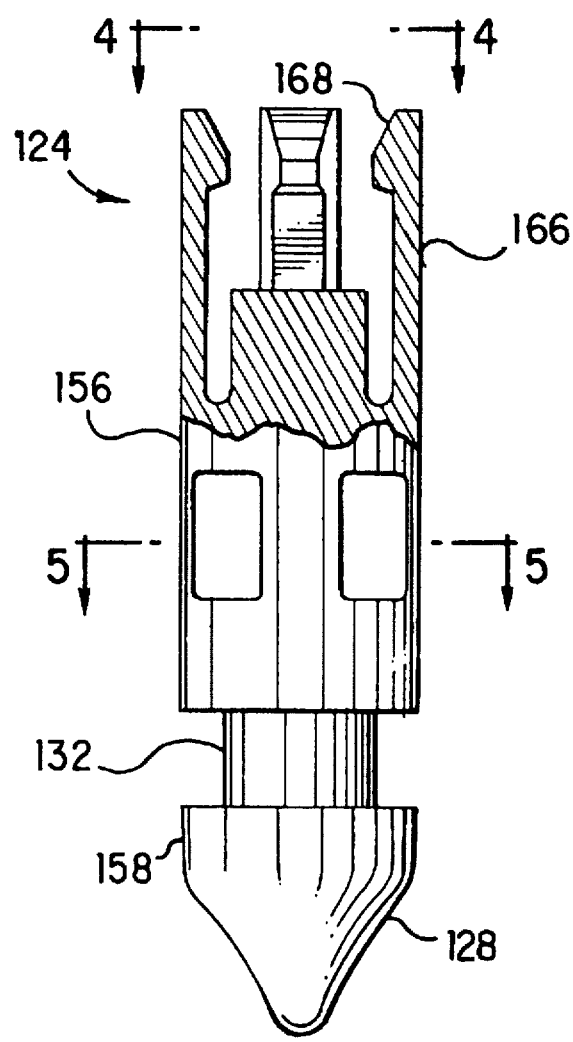
FIG. 3 is a diagrammatic isolated enlarged cross-sectional view of a plunger shown in FIG. 2.
Figure 4:
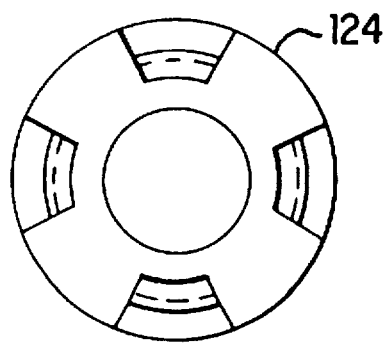
FIG. 4 is a diagrammatic end view of the plunger taken along line 4—4 of FIG. 3.
Figure 5:
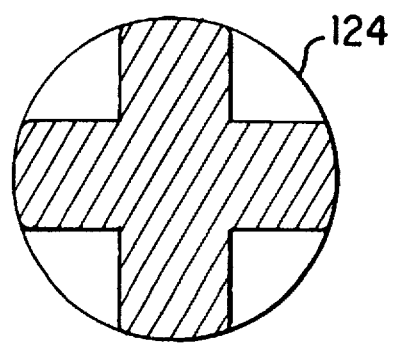
FIG. 5 is a diagrammatic cross-sectional view of the plunger taken along line 5—5 of FIG. 3.

In FIGS. 1-2, there is shown a fluid injector 100 having a nozzle body 102, a plunger/ram assembly 104, and an injector housing 106. As shown in FIG. 2, the nozzle body defines a fluid chamber or blind bore 108 and at least one orifice 110 communicating with the chamber. The fluid or ampule chamber has an end portion 112 which is, for example, tapered towards the orifice. The nozzle body and injector housing include connector means 114 for selectively attaching and removing the nozzle body to the injector housing. For example, the connector means may include external helical threads 116 formed around the nozzle body and corresponding internal helical threads formed in the injector housing.

The orifice is of a suitable diameter, length, and shape would produce a uniform jet stream under a given desired pressure range and depth of injection. Preferably for a single orifice, this diameter may be about 0.07-0.4 mm, and most preferably about 0.165 mm (0.0065 inches). If a highly precise jet stream is desired, the orifice can be formed of a synthetic gem material, such as a synthetic ruby or sapphire, as disclosed in U.S. Pat. No. 4,722,728 to Dixon. Hereinafter, the term "orifice" shall mean any type of opening, including a straight, convergent, divergent, convergent-divergent, etc.

As used in this application, the terms "proximal" or "proximally" shall denote an end or direction toward the orifice, and the terms "distal" or "distally" shall mean an end or direction longitudinally away from the orifice. The orifice may also be used to draw a fluid or liquid selected from medication or the like into the chamber. In this regard, a medication filling device such as an adapter for filling the chamber from a liquid medication supply vial directly through the orifice can be used, as described in U.S. Pat. No. 4,507,113 to Dunlap; and U.S. Pat. Nos. 4,883,483 and 4,662,878 to Lindmayer, the disclosure of which is incorporated herein by reference. Other coupling devices can also be used if desired.

The plunger/ram assembly includes a plunger assembly 120 adapted to be movably or reciprocally positioned in the chamber and a ram assembly 122 operatively connected to the plunger assembly for drawing fluid into and drawing fluid out of the chamber through the orifice.

The plunger assembly includes a plunger 124 and a seal member 126. The plunger includes a pressure wall 128 contoured to the end portion of the chamber and is received through an open end 130 portion of the chamber. The plunger assembly is positioned to reciprocally move longitudinally within the chamber to expel fluid out of the chamber via the orifice and may also draw fluid into the chamber via the orifice.

As shown in FIG. 2, the seal member is preferably is a separate member such as an o-ring positioned in a circumferential groove 132 defined in the plunger. The o-ring has an outer diameter which is slightly larger than the inner diameter of the chamber, so that the plunger assembly is in a slidingly sealing relationship with the chamber. Alternatively, the seal member may be integrally formed with the plunger such as, for example, selecting a resilient material for the plunger. The plunger assembly may also include a backup ring 134 positioned adjacent to the seal member.

As shown in FIGS. 2 and 6-8, the ram assembly includes a first driving member or pin 136, a second driving member or tip 138, a sleeve 140, and a resilient spring member or biasing member 142. These items have a generally cylindrical shape and are arranged as shown in FIG. 2. The first and second driving members are preferably spaced apart a preselected free travel distance or gap $D_1$. The plunger assembly is connected to the second driving member. Preferably, the plunger assembly is removably connected to the second driving member in order to make the plunger assembly disposable.

Preferably, the spring member is a helical compression spring. The pin is inserted into sleeve until an external annular shoulder 146 of the pin comes into contact with an internal annular shoulder 148 of the sleeve. The relative sizes and orientations of the shoulders help ensure that the pin is retained within the sleeve. An end portion 150 of the pin extends outside of sleeve. The spring is then inserted into sleeve as shown. Finally, external helical threads 152 of the tip are connected to corresponding internal helical threads 154 of the sleeve which compresses or preloads the spring member to a point where a predetermined first distance $D_1$ or spacing between the distal end of tip (second driving member) and the proximal end of the pin (first driving member) is resiliently maintained.

Figure 8:
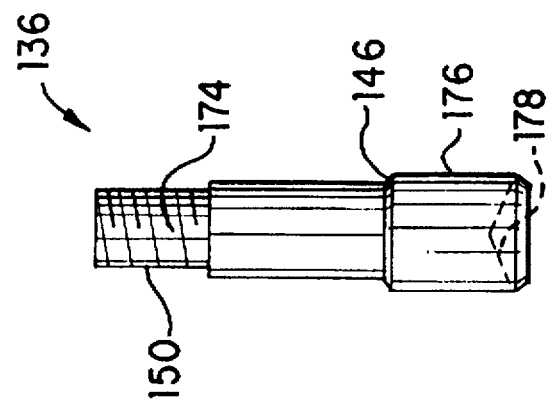
FIG. 8 is a diagrammatic isolated enlarged view of a pin or first driving member shown in FIG. 2.
Figure 7:
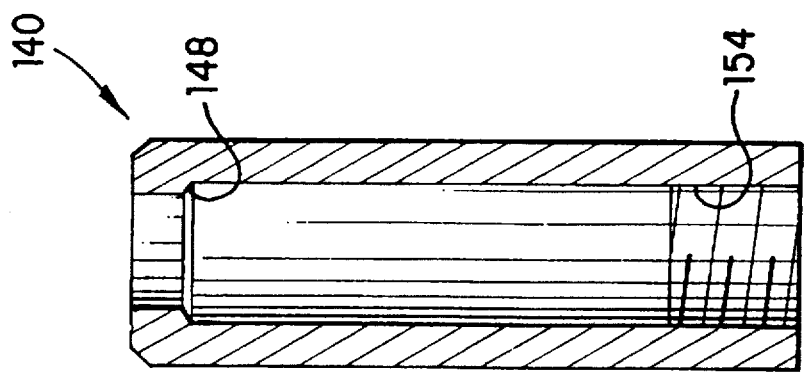
FIG. 7 is a diagrammatic isolated enlarged cross-sectional view of a sleeve shown in FIG. 2.
Figure 6:
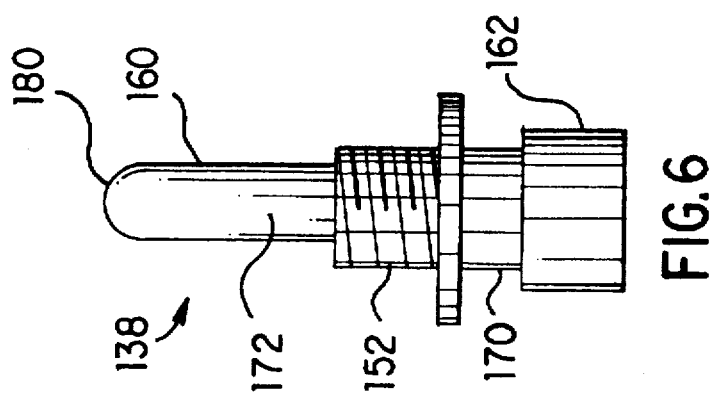
FIG. 6 is a diagrammatic isolated enlarged view of a tip or second driving member shown in FIG. 2.

As shown in FIGS. 2-3, the plunger includes a first end portion 156 facing the second driving member and a second end portion 156 facing the orifice of the chamber. As shown in FIGS. 2 and 8, the second driving member or tip includes a first end portion 160, facing the first driving member, and a second end portion 162 facing the first end portion of the disposable plunger. The first end portion of the plunger and the second end portion of the tip include releasable engagement means 164 which form a removable connection. As shown in FIGS. 2-3, the plunger preferably includes a plurality of fingers 166 having barbed ends 168 which removably attach to a circumferential groove 170 defined in the tip. The releasable engagement means cooperates with the chamber so as to be maintained in an engaged state when positioned within the chamber. Similarly, the releasable engagement means can be disengaged when it is removed from the chamber.

In this configuration, when seal member and/or plunger has to be replaced, the plunger assembly can be separated from tip. Furthermore, the tip includes a tail member 172, which is received within the spring member. As stated above, the distance between the distal end of the tail member and the proximal end of the pin constitutes the first distance $D_1$.

As shown in FIG. 2 and 8, the first driving member (e.g., pin) includes a first end portion 174 adapted to be connected to the ram 125 and a second end portion 176 facing the first end portion of the second driving member (e.g., tip). Preferably, one of the oppositely facing end portions of the first and second driving members has a concave semi-spherical surface 178. The other of the oppositely facing end portions of the first and second driving members preferably has a convex semi-spherical surface 180 which conforms to the concave semi-spherical surface. Thus, the semi-spherical surfaces are resiliently spaced apart by the resilient biasing member according the free travel distance $D_1$. As compared to planar surfaces, the semi-spherical surfaces advantageously maximize the surface area of impact or contact between the first and second driving members. This minimizes wear and/or deformation between such opposing surfaces after repeated use. Alternatively, the oppositely facing surfaces may be planar or have some other complementary shapes.

Preferably, the plunger assembly is made out of a plastic, such as polycarbonate or polypropylene, an elastomer, or a more durable material such as aluminum, stainless steel, or other metal.

Referring to FIG. 2, the nozzle body is attached to the injector housing by connecting to the external helical threads to the complementary internal helical threads defined in a front portion of the injector housing. The connection between the pin and the ram can be any conventional connection that holds the end portion of the pin to the ram, such as the threaded connection depicted. The distal end of the sleeve and the proximal end of the ram are spaced apart according to a predetermined second distance $D_2$ which is preferably selected to be greater than the first distance $D_1$. Thus, the first distance $D_1$ constitutes the controlled gap or free travel distance that the first driving member (e.g., pin) travels before impacting or otherwise moving the distal end of the second driving member (e.g., tip). Alternatively, free travel can be set by length $D_2$ being less then $D_1$. In this case, free travel can be adjusted by replacement of the pin, the length of which middle portion controls the magnitude of the free travel distance. In other words, the ram will bottom out on sleeve.

Figure 11:
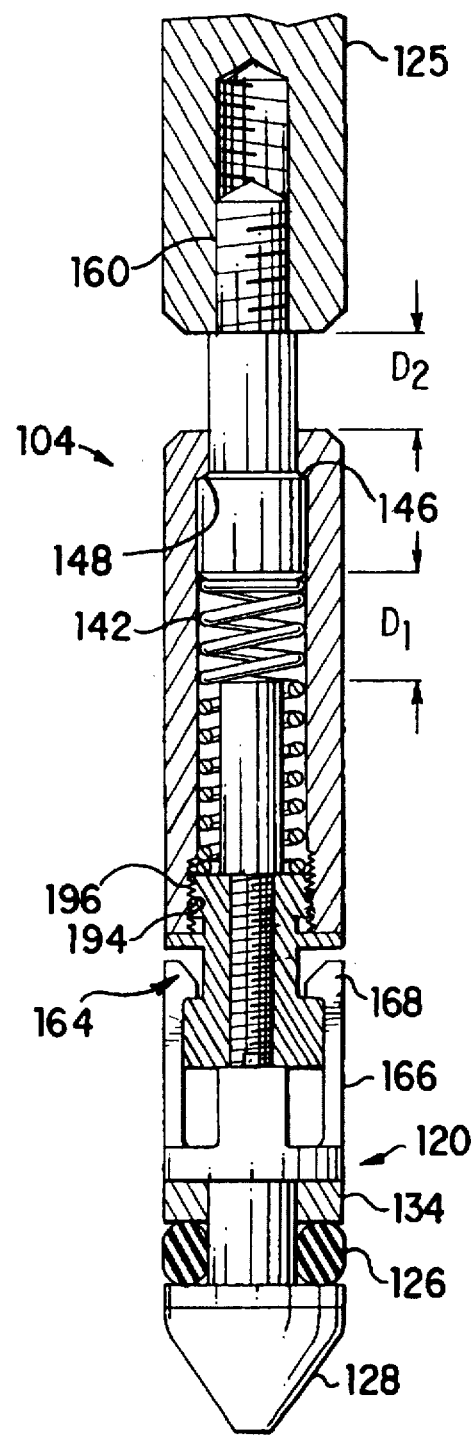
FIG. 11 is a view similar to FIG. 9 but showing the plunger/ram assembly in an assembled state and adjusted for a maximum free travel distance $D_1$.
Figure 12:
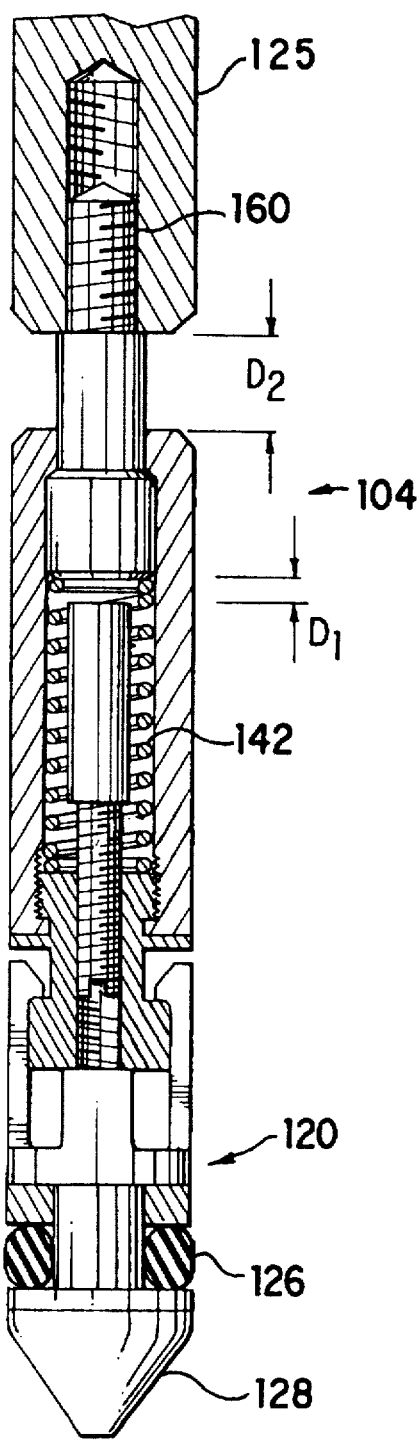
FIG. 12 is a view similar to FIG. 9 but showing the plunger/ram assembly in an assembled state and adjusted for a reduced free travel distance $D_1$.

In the second embodiment shown in FIGS. 11–18, a modified plunger/ram assembly is shown. In this arrangement, the second driving member (e.g., tip) has a means 184 for variably adjusting in situ the free travel distance $D_1$. As shown in FIGS. 10-12, the tip includes a bushing 186 having a threaded bore 188 and a tail member 190 having a threaded stem 192 movably positioned in the bore of the bushing. The bushing has external helical threads 194 that removably engage corresponding internal helical threads 196 defined on one end portion of the sleeve. A free end of the threaded stem has a slot 198 for variably adjusting the effective length of the tail member extending out of the bushing. As shown in FIG. 11, shortening the effective length of the tail member increases the free travel distance $D_1$ while lengthening the effective length of the tail member decreases the free travel distance $D_1$.

Figure 13:
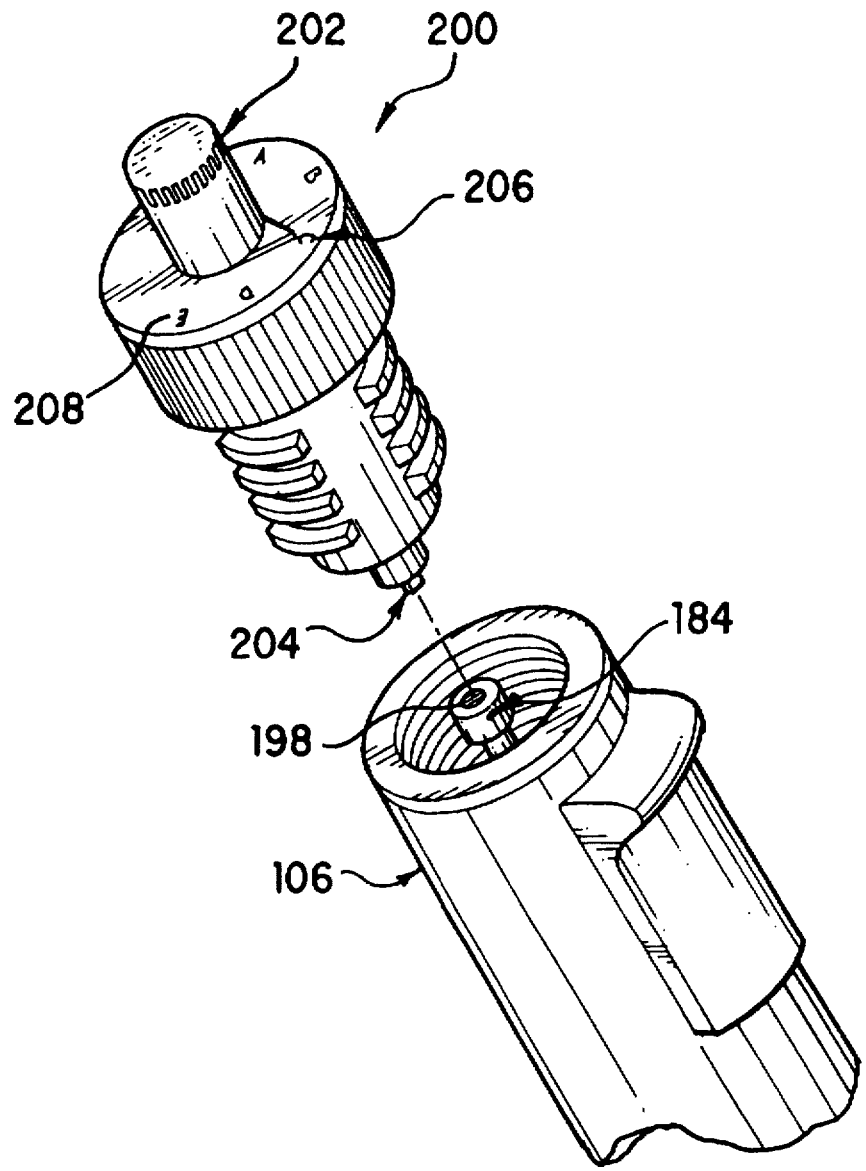
FIG. 13 is a diagrammatic exploded perspective view of an adjustment tool for adjusting the free travel distance $D_1$ of the second embodiment of the plunger/ram assembly, only partially shown.

FIG. 13 shows an adjustment tool 200 for changing the effective length of the tail portion. The adjustment tool preferably includes a knob 202 rotatively connected to a blade 204 adapted to engage the slot of the threaded stem. The tool further includes indicator means 206 such as a dial gauge 208 for measuring the displacement or effective length of the tail portion extending outside of the bushing and towards the first driving member.

The plunger/ram assembly according to the present invention is adapted for use with any fluid injector, including the hypodermic fluid injectors disclosed in the aforementioned patents, the disclosure of which is incorporated herein by reference. When a needle-type injector is to be used, the orifice is in fluid communication with the bore of an appropriately-sized needle.

Figure 14:
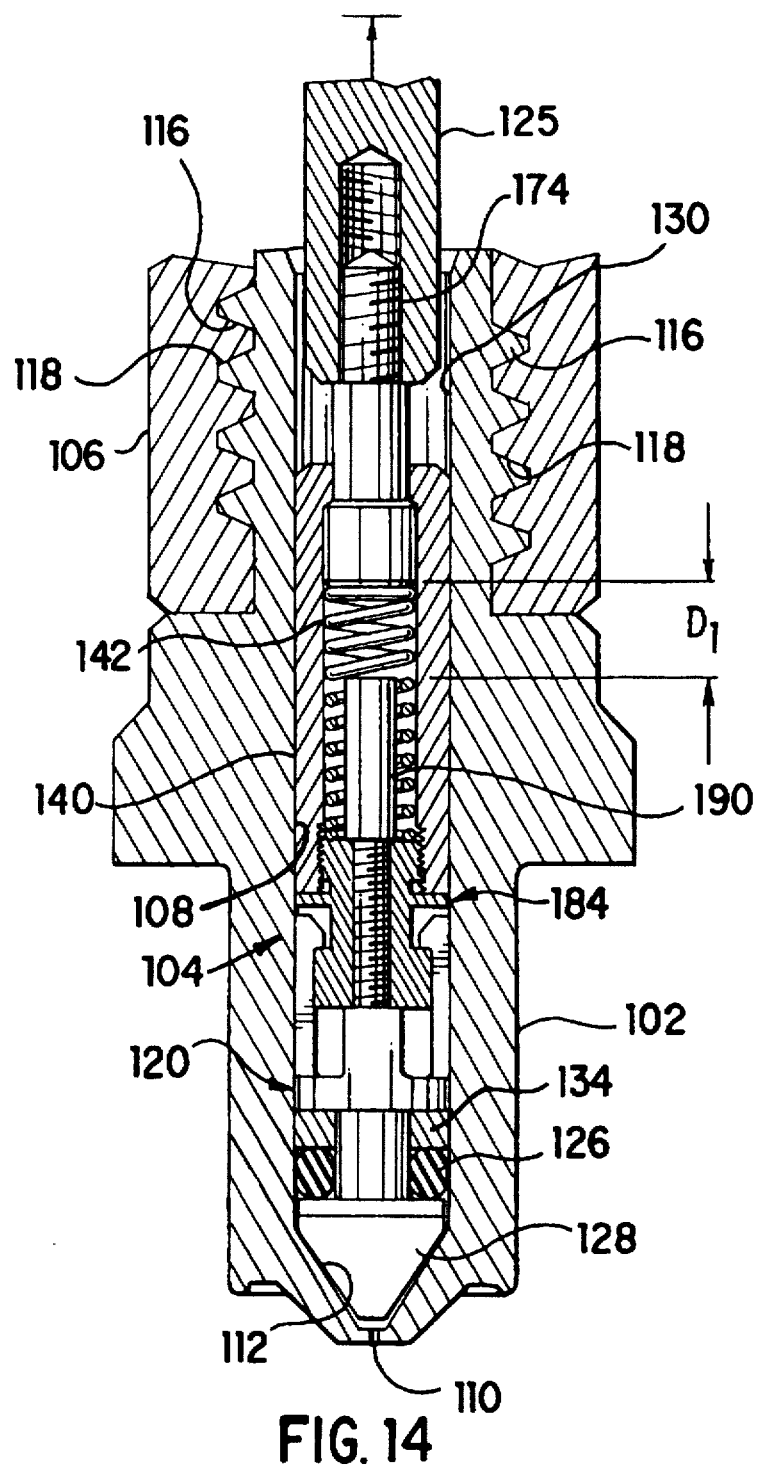
FIG. 14 is a view similar to FIG. 11 but further including a nozzle body and injector housing shown during a fill phase of operation.
Figure 15:
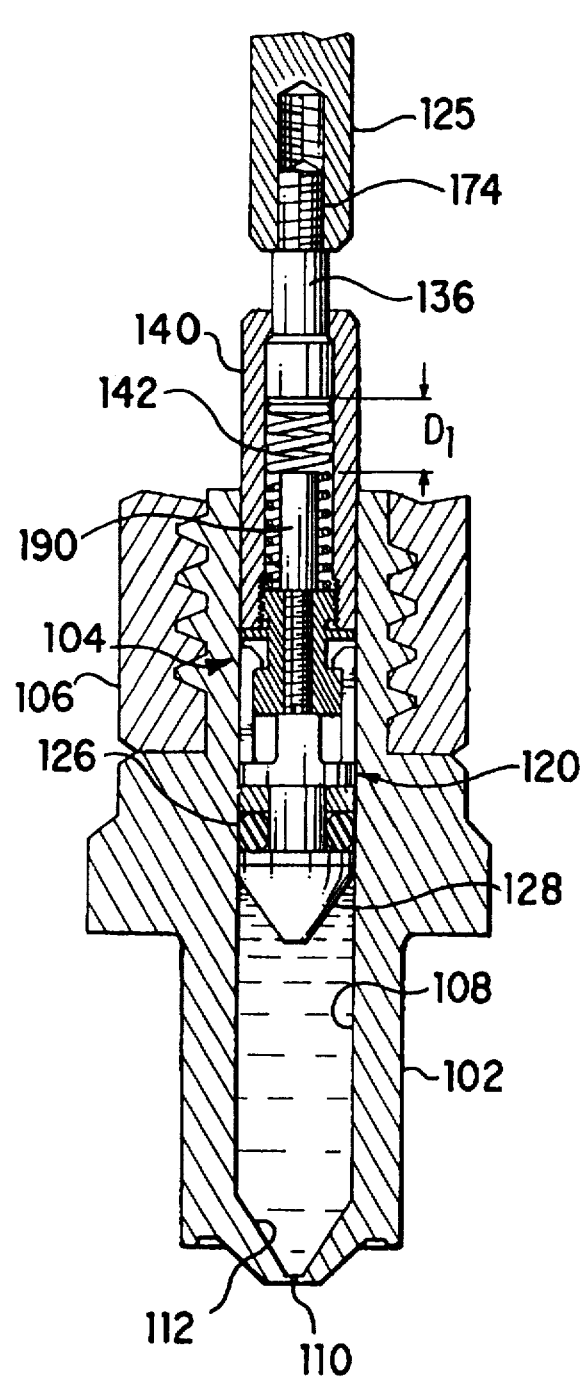
FIG. 15 is a view similar to FIG. 14 but shown during a bleed phase of operation.

Operation of the second embodiment of the plunger/ram assembly 104 will now be described with respect to FIGS. 14–18. The plunger/ram assembly is pushed proximally into the chamber, to purge air. FIG. 14 shows the plunger/ram assembly fully pushed, before the desired injection fluid is drawn into the chamber. As the plunger/ram assembly is pulled distally, a partial vacuum is established inside the chamber and the desired fluid is drawn into the chamber via the orifice, as depicted in FIG. 15.

Figure 16:
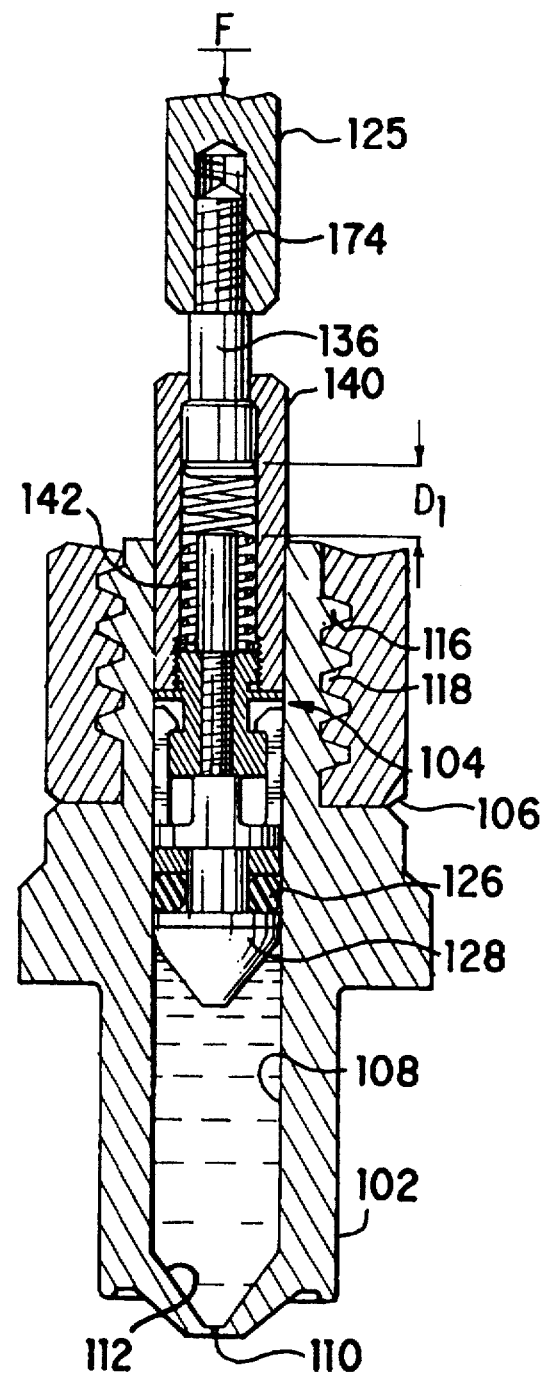
FIG. 16 is a view similar to FIG. 14 but shown during a firing initiated phase of operation.
Figure 17:
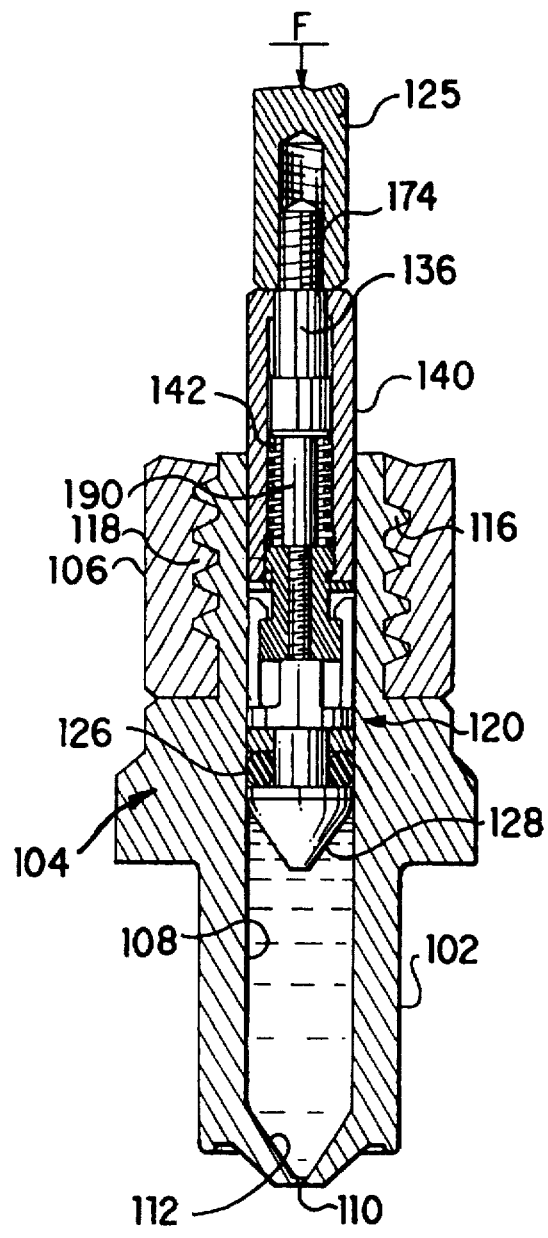
FIG. 17 is a view similar to FIG. 14 but shown during an impact gap closed phase of operation.

In the event that air bubbles and/or excess fluid are drawn into the chamber, the plunger/ram assembly must be pushed distally to expel the bubbles or excess fluid. As shown in FIG. 16, and according to a preferred embodiment of the present invention, spring member has sufficient stiffness to resist relative movement between the pin and the tip. And since the spring member is pre-loaded (being compressed within the sleeve), there is no relative movement between these two members during the bleeding or purging phase so that the gap $D_1$ or free travel distance between the first and second driving members 136,138 is maintained. It is within the ordinary skill of the art worker to select a proper resilient spring member to accomplish this purpose. Once installed, the preload on the spring member provides a force greater than the force required to move the plunger/ram assembly within the chamber and towards the orifice.

Figure 18:
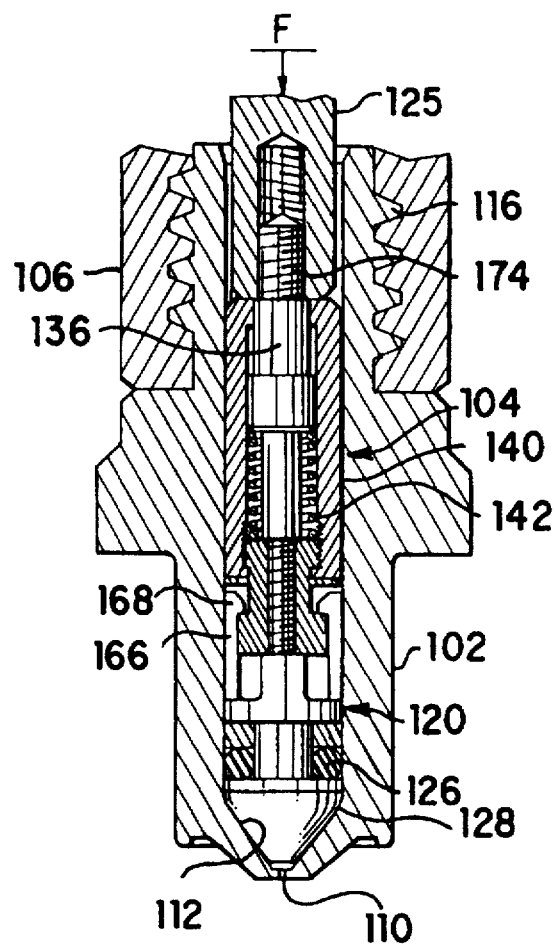
FIG. 18 is a view similar to FIG. 14 but shown during a fired phase of operation.

To inject high pressure fluid, upon application of a relatively large force F on the ram, the ram transmits this force F to the first driving member or pin. This force F compresses the resilient spring member and allows the first driving member to travel across the gap $D_1$ and directly transmit the force to the second driving member or tip. The tip thereby proximally moves the plunger towards the orifice to eject fluid out of the chamber, as shown in FIG. 18. If the plunger/ram assembly is to be reused by the same patient, the pin is pulled distally by the ram as depicted in FIG. 15 and, due to the resiliency of the spring member, the first and second distances $D_1$, $D_2$ are accurately reestablished or restored.

After fluid injection is completed, the nozzle body can be rotated until the threads are free of the corresponding threads on the injector housing so that the nozzle body can be removed from the injector housing. The plunger can be disposed of and the tip can be replaced with another tip having a tail portion of different length to change the free travel between the first and second driving members.

In a normal operation of the fluid injector, the ram of the injection device is operatively connected to an energy source and imparts a sudden force or impact F to the pin, which force is high enough to compress the spring member and to allow the pin to directly drive the tip and plunger towards the orifice. This action is sufficient to drive the fluid contained in the chamber outward through the orifice at a relatively high peak jet stream pressure of, for example, in excess of 5,000 psi. By "high pressure", what is meant is a jet stream pressure which is capable of penetrating the skin of a patient. This would be a pressure of greater than 1,000 psi and typically between about 3,000 and 10,000 psi.

The first distance or gap $D_1$ plays an important role in creating the preferred pressure spike necessary to pierce through the patient's skin or other portion of the patient's body. Changing the magnitude of the gap $D_1$, will change the initial force imparted on the tip and plunger. The peak pressure thus can be varied by varying the gap $D_1$. It can also vary depending upon the viscosity of the fluid to be injected, the desired injection penetration depth and other parameters which may affect the initial injection pressure output. One of ordinary skill in the art can determine by routine experimentation the optimum gap for any plunger assembly that is to be used with a particular injection fluid. Advantageously, tip, pin, and/or the whole ram assembly can be manufactured with different indicia such as different color codes and/or other markings, wherein each different indicia denotes a resulting predetermined length of gap $D_1$. This indicia coding scheme will easily assist the user in choosing a proper nozzle assembly for a specific application.

Also, in an alternative embodiment, the first distance $D_1$ between the distal end of the tip and the proximal end of the pin is chosen to be greater than the second distance $D_2$. In this arrangement, the sleeve functions to be directly impacted by the ram which moves the tip and plunger towards the orifice.

The nozzle body can be connected to the injector housing using any known structure for attaching and detaching two components together. The present invention preferably contemplates a bayonet mount, which has diametrically opposed threads. These threads are first aligned in an opening having a similar cross-sectional configuration provided in the injector housing so that the threads can be inserted. Thereafter, the nozzle body is rotated relative to the injector housing by a predetermined degree to prevent the nozzle body from detaching in the axial direction. The bayonet-mount enables a quick attachment and detachment of the nozzle body as well as the disposable plunger. Other connection means can be used, if desired for a particular application.

It should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention accordingly is to be defined as set forth in the appended claims.

What is claimed is:

1. A plunger/ram assembly adapted for a fluid injector having a nozzle body defining a fluid chamber, an orifice communicating with the chamber, and a ram for communicating a force to the plunger/ram assembly, said plunger/ram assembly comprising:

a plunger adapted to be movably positioned in said chamber; and a ram assembly operatively connected to the plunger for drawing fluid into and expelling fluid out the chamber through the orifice, said ram assembly including first and second driving members spaced apart by a preselected free travel distance and a resilient biasing member having a preselected preload, said plunger connected to the second driving member, said resilient biasing member operatively disposed for maintaining said free travel distance when said preload is greater the force applied to the plunger/ram assembly.

2. The plunger/ram assembly of claim 1, wherein said resilient biasing member is operatively disposed for collapsing said free travel distance when said preload is smaller than a force applied to the first driving member and when resistance of the plunger to movement is greater than the force applied to the first driving member.

3. The plunger/ram assembly of claim 2, wherein said plunger is removably connected to the second driving member.

4. The plunger/ram assembly of claim 3, wherein said plunger includes a first end portion facing the second driving member and a second end portion adapted to face the orifice of the chamber, said second driving member including a first end portion facing the first driving member and a second end portion facing the first end portion of the plunger, wherein the first end portion of the plunger and the second end portion of the second driving member include releasable engagement means which form the removable connection.

5. The plunger/ram assembly of claim 4, wherein the releasable engagement means is adapted to cooperate with the chamber so as to be maintained in an engaged state when the plunger/ram assembly is positioned within the chamber, and can be disengaged when removed from the chamber.

6. The plunger/ram assembly of claim 1, wherein when a force exceeding the preload of the resilient biasing member is applied to the first driving member in a direction towards the second driving member, the first driving member moves across said free travel distance toward the second driving member for urging the second driving member and plunger toward the orifice to expel fluid from the chamber.

7. The plunger/ram assembly of claim 6, wherein said first driving member includes a first end portion connected to the fluid infector ram and a second end portion facing the first end portion of the second driving member, one of said oppositely facing end portions of the first and second driving members having a concave semi-spherical surface, the other of said oppositely facing end portions of the first and second driving members having a convex semi-spherical surface which conforms to said concave semi-spherical surface, said semi-spherical surfaces being resiliently spaced apart by the resilient biasing member according said free travel distance.

8. The plunger/ram assembly of claim 1, wherein said resilient biasing member is a resilient spring.

9. The plunger/ram assembly of claim 8, wherein said ram assembly further includes a sleeve, said spring being disposed within the sleeve between the first and second driving members.

10. The plunger/ram assembly of claim 9, wherein said second driving member includes a tail portion facing the first driving member, said tail portion having a preselected length which controls said free travel distance.

11. The plunger/ram assembly of claim 10, wherein said tail portion of the second driving member has an adjustable length to selectively vary the free travel distance.

12. The plunger/ram assembly of claim 11, wherein said second driving member includes a bushing connected to said sleeve and having a threaded bore, said tail portion having a threaded stem movably positioned in the bore of the bushing, said threaded stem having a slot facing the plunger.

13. The plunger/ram assembly of claim 1, further including means for adjusting said free travel distance.

14. The plunger/ram assembly of claim 1, wherein said second driving member includes specific indicia indicating a corresponding predetermined resultant magnitude of said free travel distance.

15. The plunger/ram assembly of claim 14, wherein said indicia includes a preselected color code, selected from different color codes, corresponding to a respective preselected magnitude of said free travel distance.

16. The plunger/ram assembly of claim 1, further including preselected indicia marked on the ram assembly indicating a corresponding resultant preselected magnitude of said free travel distance.

17. A fluid injector, comprising:

a nozzle body defining a fluid chamber and an orifice communicating with the chamber; and a plunger/ram assembly having a ram for communicating a force to the plunger/ram assembly, said plunger/ram assembly comprising:

a plunger movably positioned in said chamber; and a ram assembly operatively connected to the plunger for drawing fluid into and expelling fluid out the chamber through the orifice, said ram assembly including first and second driving members spaced apart by a preselected free travel distance and a resilient biasing member having a preselected preload, said plunger connected to the second driving member, said resilient biasing member operatively disposed for maintaining said free travel distance when said preload is greater than the force applied to the plunger/ram assembly and for collapsing said free travel distance when said preload is smaller than the force applied to the plunger/ram assembly and when resistance of the plunger to movement is greater than the force applied to the plunger/ram assembly.

* * * * *

UNITED STATES PATENT AND TRADEMARK OFFICE
CERTIFICATE OF CORRECTION

PATENT NO. : 5,800,388

DATED : September 1, 1998

INVENTOR(S) : David SCHIFF et al.

It is certified that error appears in the above-identified patent and that said Letters Patent is hereby corrected as shown below:

At column 7, line 55 (claim 1, line 16): after "greater" insert --than--.

Signed and Sealed this

Twenty-second Day of December, 1998

Attest:

BRUCE LEHMAN

Attesting Officer     Commissioner of Patents and Trademarks